United States Patent [19]
Duffy et al.

[11] Patent Number: 5,941,846
[45] Date of Patent: Aug. 24, 1999

[54] METHOD AND APPARATUS FOR POWER CONNECTION IN A MODULAR PATIENT CARE SYSTEM

[75] Inventors: Robert J. Duffy, Poway; Lon M. Severe, San Diego; Edward M. Richards, Pleasanton; Shawn W. DeKalb, San Diego; James P. Stewart, El Cajon, all of Calif.

[73] Assignee: Alaris Medical Systems, Inc., San Diego, Calif.

[21] Appl. No.: 08/871,307

[22] Filed: Jun. 9, 1997

Related U.S. Application Data

[63] Continuation-in-part of application No. 08/403,503, Mar. 13, 1995, Pat. No. 5,713,856.
[51] Int. Cl.⁶ .................................................. A61M 31/00
[52] U.S. Cl. ............................................................ 604/65
[58] Field of Search ................................ 604/30–34, 49, 604/65–67; 128/DIG. 12, DIG. 13

Primary Examiner—John D. Yasko
Assistant Examiner—Manuel Mendez
Attorney, Agent, or Firm—Pennie & Edmonds LLP

[57] ABSTRACT

A modular patient care system having a central management unit module and one or more detachable functional units is described. Using unique mechanical and electrical features, the modular patient care system is capable of flexibly, bilaterally, and safely providing electrical power from the central management unit to the attached functional units, with exposed power leads of end units being electrically isolated for safety and security. Functional units are capable of detecting the presence of other functional units more distant from the central management unit for passing power to those units, and for otherwise electrically isolating exposed power leads when no further units are attached. Additionally, the modular patient care system provides for a modular connection arrangement wherein modules are detachably connected to each other in a convenient, flexible, interchangeable, and secure manner by providing a hinge connector pair, a specially located latch mechanism, and a guide means between any pair of modules.

27 Claims, 8 Drawing Sheets

METHOD AND APPARATUS FOR POWER CONNECTION IN A MODULAR PATIENT CARE SYSTEM

CROSS REFERENCE TO RELATED APPLICATIONS

This application is a continuation-in-part of U.S. patent application Ser. No. 08/403,503, entitled "Modular Patient Monitoring and Infusion System," filed Mar. 13, 1995, now U.S. Pat. No. 5,713,856 and assigned to the assignee of the present invention. The subject matter of U.S. patent application Ser. No. 08/403,503, now U.S. Pat. No. 5,713,856 is incorporated herein by reference.

This application also contains subject matter related to copending U.S. Pat. App. Ser. No. 08/866,664 filed Jun. 9, 1997 entitled "Method and Apparatus for Logical Addressing in a Modular Patient Care System," both assigned to the assignee of the present invention. The subject matter of this application is also incorporated herein by reference.

FIELD OF THE INVENTION

The present invention relates generally to modular patient care systems. More specifically, the present invention relates to modular connection arrangement wherein modules are detachably connected to each other in a convenient, flexible, interchangeable, and secure manner. Additionally, the present invention relates to a scheme for flexibly, bilaterally, and safely providing electrical power from a central management unit to attached peripheral units.

BACKGROUND OF THE INVENTION

Systems containing multiple infusion pumping units, sensing units such as blood pressure monitors and pulse oximeters, and other patient-care units are known in the medical field. For example, Kerns et al (U.S. Pat. No. 4,756,706; "Kerns") discloses a centrally managed pump system in which pump and monitoring modules are selectively attached to a central management unit. The central management unit controls the internal setup and programming of the attached modules, and receives and displays information from them. Each module is capable of being detached from the central management unit except for the first module, which is permanently attached. Once attached and programmed, a module which is subsequently detached is still capable of operating independently of the management unit.

Figure 1:
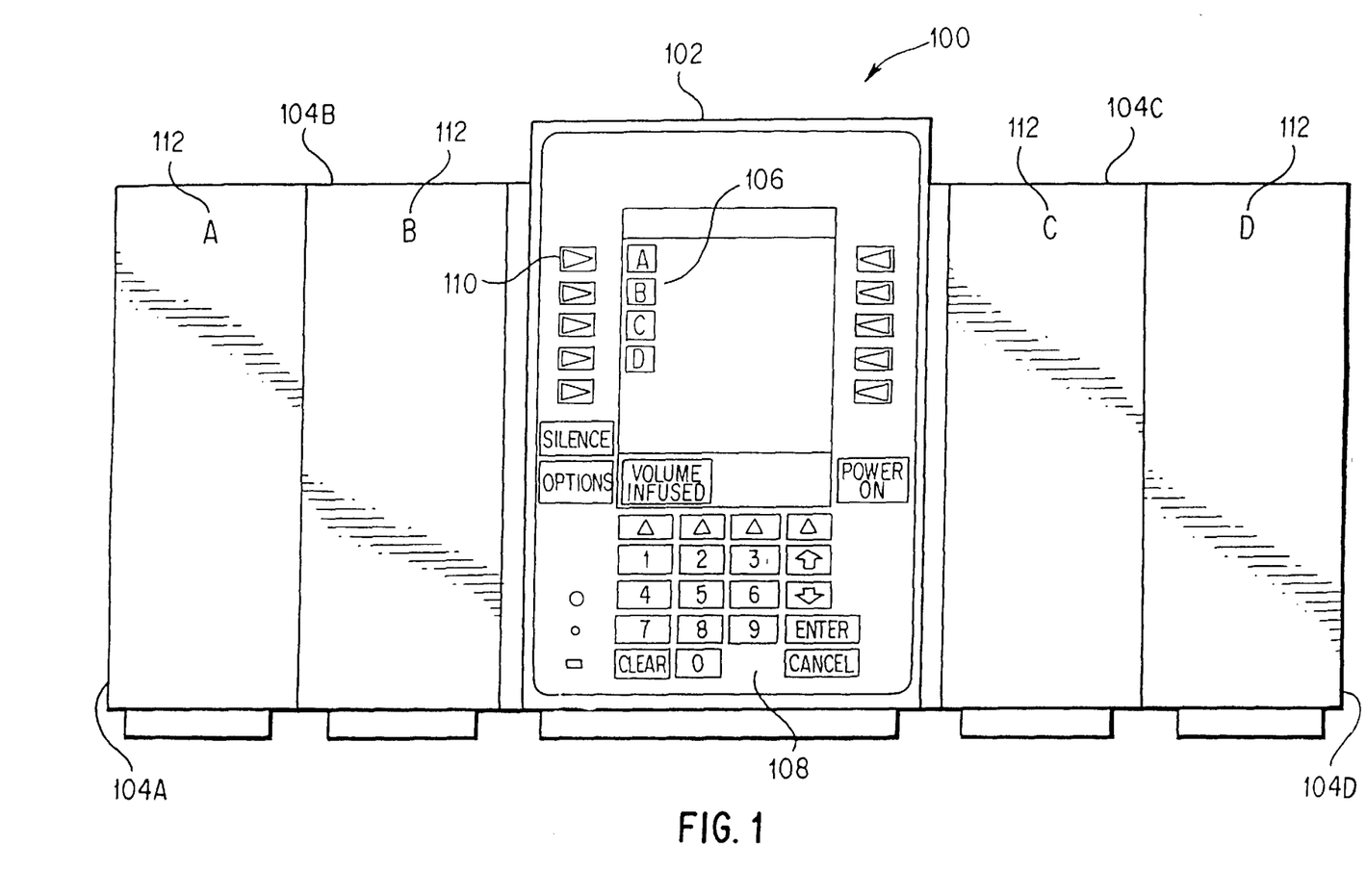
FIG. 1 is a front view of a multi-module electronic system wherein the individual modules are interconnected electrically and structurally in accordance with the present invention.

Kerns provides for attachment of the modules in a vertical stacking sequence in a manner similar to that shown in FIG. 1. Attachment of an additional unit to the modular patient care system involves a multiple step process. These steps include (1) sliding a support plate 62 of the additional unit into the channel 64 of a previous unit, and (2) turning a knob 120, causing male connectors 122 and 124 of the additional unit to pop up and mate with corresponding female portions in the previous unit (Kerns FIG. 3 and col. 4 lines 7–16). Thus, achieving mechanical and electrical connectivity in Kerns clearly involves a multi-step, two-handed operation.

Further, Kerns provides for distinct, direct electrical connectivity from each stack module to the central management unit. Each module is provided with a separate AC power signal from the central management unit AC+ and AC– leads. Each module also contains its own power supply for autonomous operation when disconnected from the central management unit (Kerns FIG. 6).

Kerns has several disadvantages. First, for electrical and mechanical connectivity of an added unit to the central management unit, a multi-step, two-handed operation is needed, which may be cumbersome and time consuming in the medical environment. Second, because each module requires its own set of electrical paths to the central unit, the total number of modules which may be stacked is only one greater than the number of pass-through cables in each module. For example, for the pass-through structure shown in Kerns FIG. 4f, only four modules total may be accommodated by a system which uses these modules. Third, there is added weight, cost, and complexity due to the multiple cabling structure. For example, each signal of each cable must have its own contact pin in among the pins 122 of the contact structure of Kerns FIG. 3. Finally, the presence of a power supply in each functional module adds weight and cost.

Rubalcaba (U.S. Pat. No. 4,898,578) also discloses a drug infusion system which includes a plurality of infusion pump modules selectively attached to a central management unit so as to provide for centralized control. In particular, the central management unit obtains infusion parameters from the user and then performs calculations with the parameters to establish the desired infusion rate. Once this rate is determined, the central management unit may control the infusion accordingly. Rubalcaba, however, provides no solution for the problems related to electrical and mechanical connectivity of units described above with respect to Kerns.

Accordingly, it is an object of the present invention to provide a modular patient care system wherein modules are detachably connected to each other in a convenient, flexible, interchangeable, and secure manner.

It is another object of the present invention to provide a modular patient care system wherein each functional unit is powered by the central management unit using a common power bus scheme to avoid a multiplicity of power lines.

It is a further object to provide a flexible, bilateral power scheme wherein any functional unit may be placed anywhere in a linear array of units and be adequately powered. It is a further object of the present invention to make this powering scheme safe by avoiding active power supply voltages at exposed ends of the power bus.

SUMMARY OF THE INVENTION

These and other objects of the present invention are provided in a modular patient care system comprising an interface unit for providing a user interface to the system and for providing electrical power to at least one functional unit, the functional unit being capable of removable connection to the interface unit for providing patient therapies or monitoring the condition of the patient, the functional unit being for removable attachment to the interface unit or other functional units so as to form a linear array of units. The linear array of units comprises an originating end and a terminating end, and each unit has an originating side and a terminating side, the originating side of any unit being capable of removable connection to the terminating side of any other unit. In one embodiment, the originating side is the left side, and the terminating side is the right side of the linear array.

The interface unit according to the present invention has a left power lead for powering left side functional units and a right power lead for powering right side functional units. Power supply aspects of the left and right sides are substantially symmetric. Using the left side as an example, power supplying aspects of the interface unit are arranged so as to connect power to the left power lead when functional units are attached to the left, but to leave the left power lead electrically isolated when no functional units are attached to the left. This prevents the unsafe and insecure situation of a live voltage existing at an exposed left power lead of the linear array of units, which would be subject to shorting out or otherwise undesirably discharging. To accomplish this objective, the interface unit includes a power source for receiving electrical power from a power supply and providing electrical power, a detecting lead for detecting the presence of a right sense signal, such as a ground signal, from a unit attached to the left, means for coupling the power source to the left power lead in the presence of the right sense signal, and means for decoupling the power source from the left power lead in the absence of the right sense signal. In one embodiment, the detecting lead is connected to a gate of a field effect transistor, the power source is connected to a drain of the field effect transistor, and the left power lead is coupled to a source of the field effect transistor.

A flexible, bilateral, and safe powering scheme in the modular patient care system according to the present invention is also provided for by providing an exemplary functional unit having a left lead and a right lead, the left lead for contacting the right lead of a left adjacent functional unit or the right power lead of the left adjacent interface unit in the linear array, the right lead for contacting the left lead of a right adjacent functional unit in the linear array or the right power lead of the right adjacent interface unit in the linear array. The functional unit has a load unidirectionally coupled to the left and right leads and capable of receiving electrical power from either of the leads. The functional unit also has a right sense signal lead for providing a right sense signal to the adjacent right unit, if any, and a left detect lead for detecting the right sense signal from the adjacent left unit, if any. Further, the functional unit also has a left sense signal lead for providing a left sense signal to the adjacent left unit, if any, and a right detect lead for detecting the left sense signal from the adjacent right unit, if any. Finally, the functional unit comprises means for bidirectionally connecting the left power lead to the right power lead only upon detecting both left and right signals.

In this manner, a functional unit which is located between two other units in the linear array is capable of powering its load while also passing power, in either direction as needed, to the adjacent unit which is located farther away from the interface unit. However, if the functional unit is located at the left end of the linear array, the left power lead remains electrically isolated because no right sense signal is detected. Likewise, if the functional unit is located at the right end of the linear array, the right power lead remains electrically isolated because no left sense signal is detected. In this manner, the functional units are capable of flexible, bilateral power connection in the linear array of units, and live power contacts are prevented from existing at the leads located at the ends of the linear array of units for safety and security.

In another embodiment of the invention, a modular patient care system is provided having an interface module for providing a user interface to the system and at least one functional module capable of removable connection to the interface module. The functional module is for providing patient therapies or monitoring the patient's condition and is capable of removable attachment to the interface module or other functional modules so as to form a linear array of modules. The linear array of modules comprises an originating end and a terminating end, and each module has an originating side and a terminating side, the originating side of any module being capable of removable connection to the terminating side of any other module.

Physically, an exemplary functional module according to the present invention comprises a first portion grippable by a user and is configured and dimensioned so as to be capable of being held by a single hand of the user by gripping the first portion. Any pair of modules, including for example the interface module and the exemplary functional module, are easily, flexibly, and interchangeably coupled by including a hinge connector pair for allowing hingeable engagement of the pair, a latch mechanism for securing the pair together, and a guide mechanism located between the hinge connector pair and the latch mechanism for discouraging off-axis engagement of the modules and for providing mechanical stability to the engaged pair. The latch mechanism is designed to automatically secure the pair together, such that engagement of the modules takes place in a single-handed, single step operation, but is designed to require a manual operation by a hand separate from the hand gripping the first portion to unlatch the modules during disengagement. This provides for increased security and prevention of accidental disengagement of modules. Preferably, the latch mechanism springably couples together such that tactile feedback is provided to the user during attachment. An optional fastener for fastening the latching mechanism together may be included, which requires a special tool for unfastening the latching mechanism so as to further increase system security at the option of the user.

DETAILED DESCRIPTION OF THE INVENTION

The following embodiments of the present invention will be described in the context of a modular patient care system, although those skilled in the art would recognize that the disclosed methods and structures are readily adaptable for broader application. Note that whenever the same reference numeral is repeated with respect to different figures, it refers to the corresponding structure in each figure.

FIG. 1 discloses a modular patient care system 100 in accordance with the present invention. Modular patient care system 100 comprises a plurality of modules or units, including interface unit 102 and functional units 104, detachably coupled to each other to form a linear array. Shown in FIG. 1 are exemplary functional units 104A, 104B, 104C, and 104D coupled to interface unit 102. While four functional units are shown in FIG. 1, a modular patient care system in accordance with the present invention may comprise interface unit 102 coupled to only a single functional unit 104, or may comprise interface unit 102 coupled to as many as "N" functional units 104.

Interface unit 102 generally performs the functions of (1) providing a physical attachment of the system to structures such as IV poles and bedrails, (2) providing electrical power to the system, (3) providing an interface between the system and external devices, (4) providing a user interface to the system, and (5) providing overall system control, which includes providing information to and receiving information from functional units 104. Shown in FIG. 1 are certain user interface aspects of interface unit 102, which may include an information display 106, numerical hardkeys 108, and softkeys 110.

Functional units 104 are generally for providing patient therapies or monitoring responsive to information, at least some of which may be received from interface unit 102. In many cases, functional units 104 are also for communicating information to interface unit 102. For example, functional unit 104A may be an infusion pump unit for delivering fluids to a patient responsive to certain commands received from interface unit 102, while functional unit 104B may be a blood pressure monitoring unit for providing patient blood pressure information to the interface unit 102. The scope of the invention is not so limited, however.

For the purposes of the present invention, the specific function of each individual functional unit 104 is not critical. Rather, the present invention is directed toward (1) the mechanical and electromechanical coupling of the functional units 104 to each other and to interface unit 102, and (2) the electrical powering scheme of the modular patient care system 100. Thus, for purposes of understanding the present invention, it is important only to recognize that functional units 104 (1) require means for detachably coupling to each other and to interface unit 102, and (2) require electrical power.

In a preferred embodiment of the present invention, interface unit 102 and functional units 104 are laterally interchangeable. By laterally interchangeable, it is meant that the modules may be placed in any order in forming a linear array of modules. Thus, in FIG. 1, the modular patient care system 100 may instead have its modules ordered left-to-right in the sequence 104C, 102, 104B, 104D, 104A without affecting its functionality. In order to be laterally interchangeable, the units 102 and 104 of FIG. 1 should have substantially identical interconnection features on their respective left sides, and should have corresponding substantially identical interconnection features on their right sides. If the units were instead for coupling in a vertical linear array, which is within the scope of the present invention, the interconnection features would have substantially identical interconnection features on their respective top sides, and would have corresponding substantially identical interconnection features on their bottom sides. For clarity of explanation, however, only a left-to-right physical arrangement is described.

To achieve the lateral interchangeability described above, each of the units 102 and 104 should also have power, unit detection, and communication circuitry which is complementary. By complementary, it is meant that the units 102 and 104 generally have power, unit detection, and communications circuit contacts on a first side and on a second side, and that the first side contacts of one unit may be connected to corresponding second side contacts of any other unit, with the overall linear array of units comprising modular patient care system 100 being fully operational. In FIG. 1, for example, the first side of a unit is the left side, and the second side of a unit is the right side. Further to this example, and as further explained later, functional unit 104C must be capable of receiving electrical power from interface unit 102 to its left and transferring it to unit 104D to its right; yet, if physically interchanged with functional unit 104B, unit 104C must be capable of receiving electrical power from interface unit 102 to its right and transferring it to unit 104A to its left, and so on.

As shown in FIG. 1, each functional unit 104 may include a unit ID indicator 112 which identifies a logical address of the functional unit within the linear array. The logical address of a functional unit 104 indicates its position in the linear array relative to other functional units 104. The logical address of a functional unit 104, such as unit 104B, is used by the interface unit 102 to identify and uniquely communicate with functional unit 104B in a common communications bus environment to be described later. In a preferred embodiment of the invention, the logical address of a functional unit corresponds to its sequential position in the linear array of functional units. Thus, the system shown in FIG. 1 may illustratively contain functional units 104A–104D with logical addresses A, B, C, and D, ordered left to right. In this embodiment, the left side of the leftmost unit forms an originating end of the linear array, while the right side of the rightmost unit forms a terminating end of the linear array.

Figure 2:
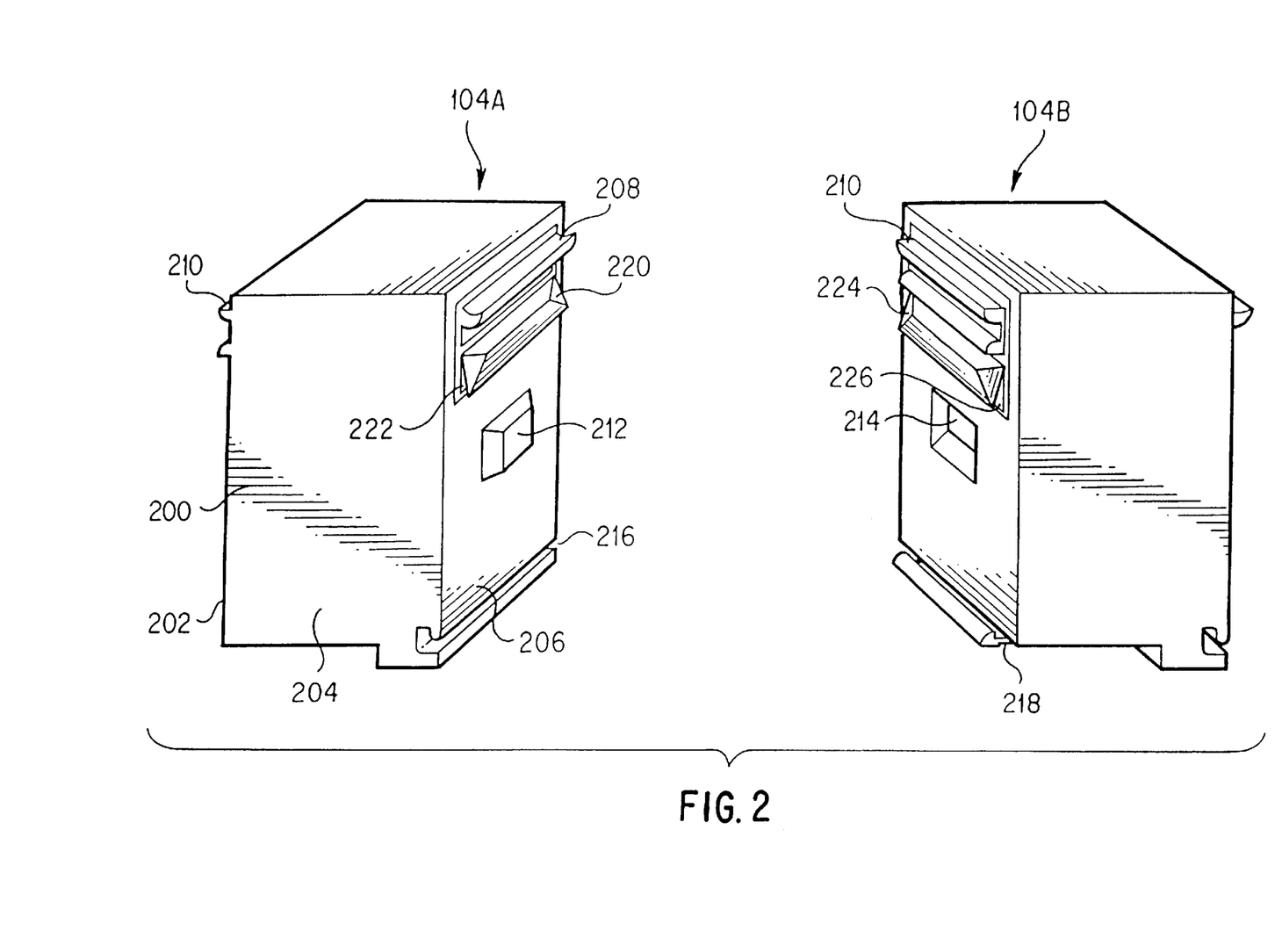
FIG. 2 shows an oblique view of two modules showing structural and electrical features for module connection in accordance with the present invention.
Figure 3A:
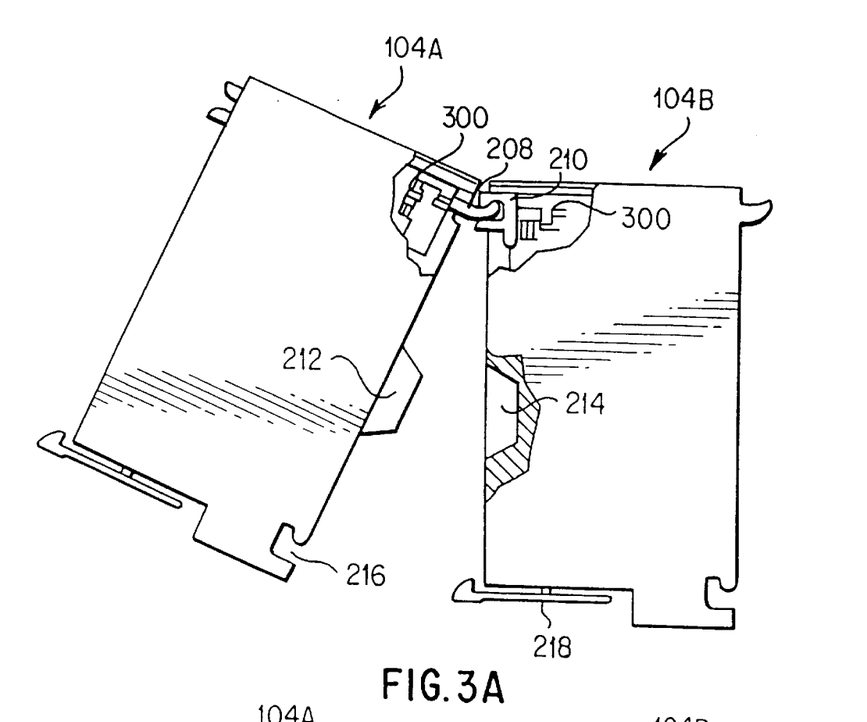
FIG. 3a shows a front view of the modules shown in FIG. 2 positioned for subsequent engagement with each other, with portions broken away to reveal the connection scheme according to the present invention and associated electronic components.
Figure 3B:
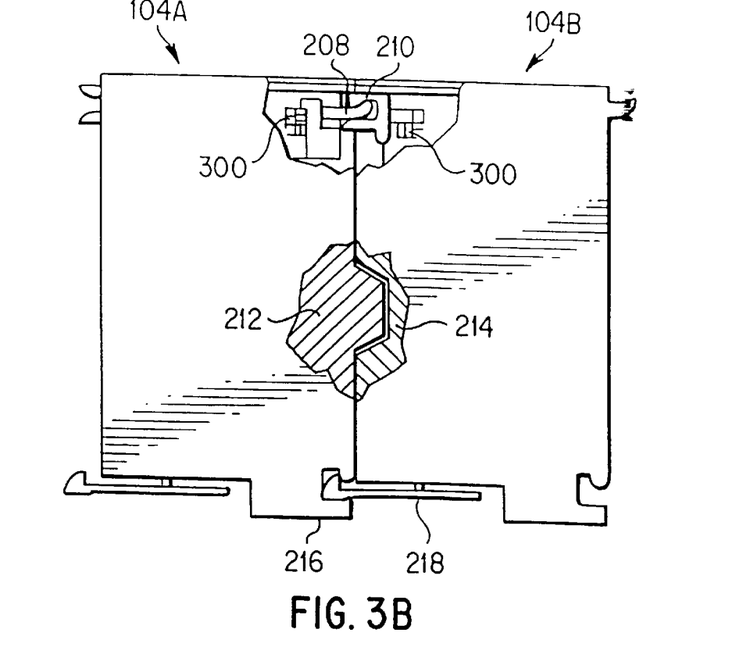
FIG. 3b shows the modules of FIG. 3a after engagement.
Figure 4:
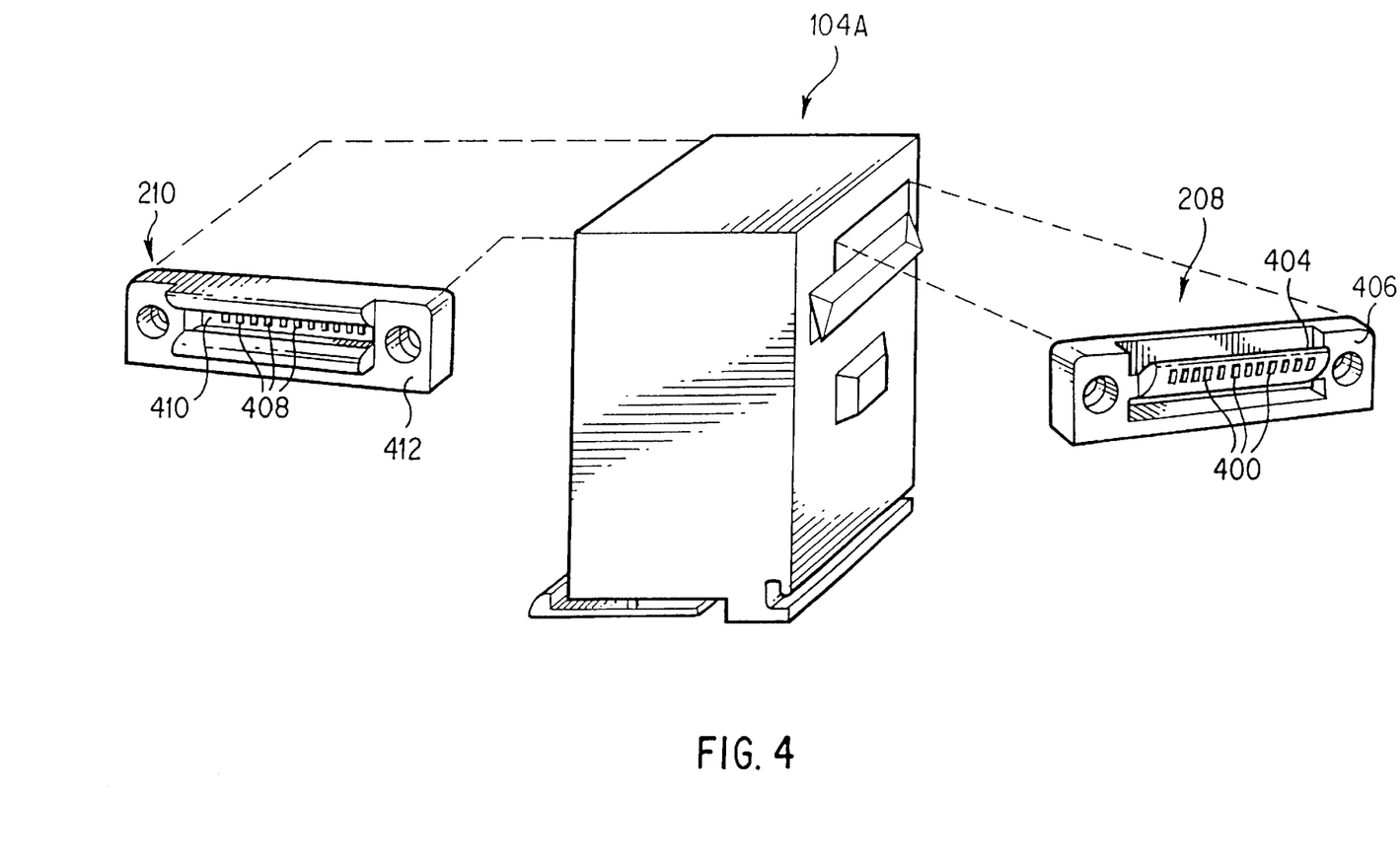
FIG. 4 shows an exploded perspective view of a single module showing the interconnector parts of the present invention enlarged and out-of-scale.

Referring now to FIGS. 2 through 4, the mechanical and electromechanical aspects of interface unit 102 and functional units 104 as designed in accordance with a first embodiment of the present invention are now described. For purposes of the first embodiment of the present invention, interconnection features of interface unit 102 are substantially identical to interconnection features of functional units 104. Therefore, only an exemplary unit 104A will be described. Also, an exemplary unit 104B, substantially identical to unit 104A and for connecting thereto, will be described when needed for clarity.

FIG. 2 shows an oblique representation of exemplary units 104A and 104B positioned before being matably connected, while FIGS. 3a and 3b show appropriate cutaway views of units 104A and 104B during and after the connection process, respectively.

As shown in FIG. 2, unit 104A comprises a chassis 200 having a left side 202, a front 204, and a right side 206. It is to be appreciated that although FIG. 2 shows numbered components on units 104A and 104B according to their visibility in the oblique drawing, the units 104A and 104B contain substantially identical numbered components. Unit 104A further comprises a male connector portion 208 on right side 206, a female connector portion 210 on left side 202, a male elevation feature 212 formed on right side 206, a female recess feature 214 formed in left side 202, a catch feature 216 formed near the bottom of right side 206, and a latch 218 near the bottom of left side 202. Unit 104A further comprises cover 220 tethered to male connector portion 208 for covering the male connector portion 208 during periods of non-use, and pocket 222 formed in right side 206 near male connector portion 208 for receiving cover 220 otherwise. Unit 104A further comprises cover 224 tethered to female connector portion 210 for covering female connector portion 210 during periods of non-use, and pocket 226 formed in left side 202 near female connector portion 210 for receiving cover 220 otherwise.

Generally, as shown in FIGS. 3a and 3b, units 104A and 104B are designed to be connected using the steps of (1) tilting the units relative to each other while inserting male connector portion 208 into female connector portion 210, (2) swinging down the units to a nearly parallel position such that male elevation feature 212 is received into female recess feature 214 and latch 218 is received into catch feature 216, and (3) pressing the units together such that latch 218 is locked into catch feature 216.

Male connector portion 208 of unit 104A is positioned and formed for hingeable connection with female connector portion 210 of unit 104B for achieving mechanical and electrical coupling of units 104 and 105. In a preferred embodiment of the invention, male connector portion 208 and female connector portion 210 also form a 15-pin electrical connector pair for electrically coupling. This electrical connector pair is for electrically coupling electronic components contained in units 104A and 104B, these electronic components being shown generally as elements 300 in FIGS. 3a and 3b. The geometry of male connector portion 208 and female connector portion 210 include lead-in and chamfer to reduce the probability of dropping and off-axis insertion. Advantageously, the geometry of the male-female pair is designed to prevent a unit from falling off if it is hooked but not yet latched. The mechanical characteristics of the male-female pair are detailed in U.S. patent application Ser. No. 08/403,502, cross-referenced above.

Male elevation feature 212 is formed on right side 206 of unit 104A for mating with female recess feature 214 formed in left side 202 of unit 104B to provide multiple contact surfaces for improved front to back stability during vibration of the connected units. Further, the geometry of male elevation feature 212 includes lead-in and chamfer for mechanical guidance into recess feature 214 such that the probability of off-axis insertion is reduced.

Latch 218 is for engaging a catch feature 216 during connection. This keeps the units together mechanically after attachment. In a preferred embodiment, latch 218 is spring loaded with a pre-load force sufficient to positively engage the catch feature 216, close, and remain latched unless disengaged by an operator. Also in a preferred embodiment, techniques known in the art may be used to shape latch 218 and catch feature 216 such that a small vibration resonates through units 104A and 104B upon attachment, to provide tactile feedback to the user.

Cover 220 is for covering male connector portions 208 during transport and periods of non-use. In a preferred embodiment of the invention, cover 220 is made of an elastomeric material which is elastic and waterproof. Cover 220 is tethered to male connector portion 208 to reduce the possibility of being lost or misplaced by the user, and is dimensioned and configured to be swung up and over male hook feature 208 for protection. Pocket 222 is formed in right side 206 beneath male connector portion 208 for receiving cover 220, which nests into pocket 224 when not in use. Cover 220 may be swung up out of pocket 222 to cover male connector portion 208 to protect connector portion 208 from dust or fluids. Similar purpose, material, and configurations apply to cover 224 and pocket 226.

Advantageously, the covers 220 and 224 and pockets 222 and 226 are configured and dimensioned such that the covers recess flush yet are partially compressed when the units 104A and 104B are attached, thus providing additional shock cushioning and preventing rattling during vibration or transport.

In a preferred embodiment of the invention, the size and geometry of unit 104A is generally such that it may be held by a single hand of a user, although the invention is not necessarily so limited. This is generally the same user hand which receives the tactile feedback described above upon unit attachment.

FIG. 4 shows a view of unit 104A exploded to more succinctly show male connector portion 208 and female connector portion 210 with respect to a preferred embodiment of the invention. Specifically, male connector portion 208 comprises electrical contacts 400 contained on a curved lip 404 formed on a body portion 406. Further, female connector portion 210 comprises electrical contacts 408 protruding into an aperture 410 formed in body portion 412. In a preferred embodiment of the invention, the contact geometry and orientation of electrical contacts 400 and 408 may allow a first set of individual electrical contact pairs formed by joining the connectors to make electrical connection prior to a second set of electrical contacts during connection. A result of this geometry and orientation will be that the first set of contacts will also break after the second set of contacts during disconnection. This ensures, for example, that an electrical ground connection between the units may made first during module attachment, creating a path to dissipate electrostatic discharge.

Also in a preferred embodiment of the invention, body portions 406 and 412 are made of a low surface energy/hydrophobic material to shed fluid from exposed surfaces. Also, an a preferred embodiment the electrical contacts 400 and 408 are insert-molded into body portions 406 and 412, which prevents extraneous fluids from accumulating adjacent to electrical connections.

Figures 5A, 5B:
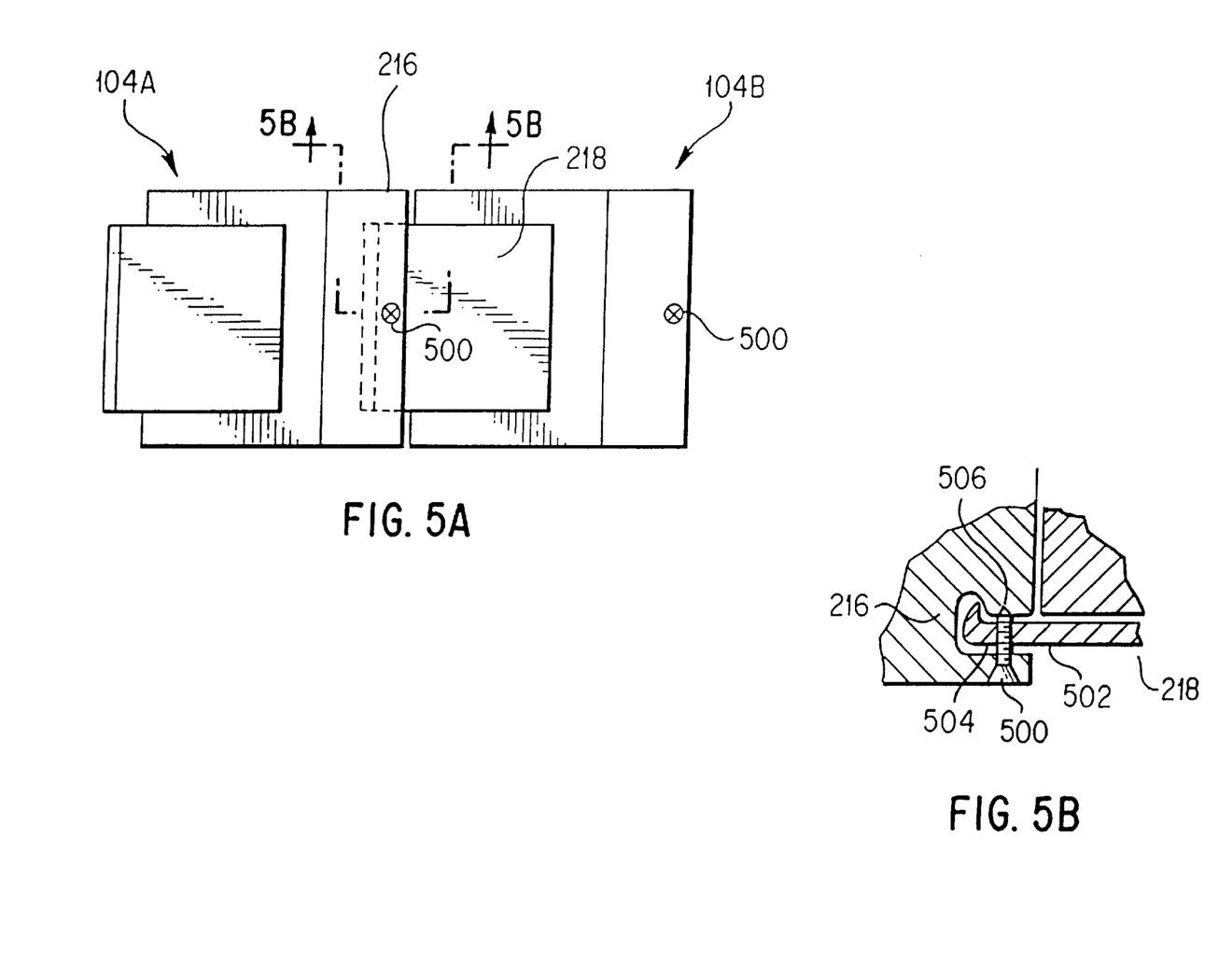
FIG. 5a shows a bottom view of a pair of engaged modules in accordance with an embodiment of the present invention.
FIG. 5b shows a front cut-away view of the modules of FIG. 5a to reveal a latching and locking scheme in accordance with an embodiment of the present invention.

FIGS. 5A and 5B show units 104A and 104B with additional features in accordance with a preferred embodiment of the invention. FIG. 5A shows a bottom view of coupled units 104A and 104B. Unit 104B comprises latch 218 for engaging catch feature 216 of unit 104A. In this embodiment however, a fastener 500 may be employed to provide a means for making the attachment of units 104A and 104B permanent until the fastener 500 is released by a user using a releasing technique. This releasing technique may employ the use of a special tool (not shown) made available only to specified users. FIG. 5B shows a side view of latch 218 engaged to catch feature 216, further showing a latch tongue 502 of latch 218 which forms a hole 504 in an area which overlaps catch feature 216. Fastener 500 which is, for example, a screw, is inserted from the bottom of functional unit 104A near catch feature 216 through hole 504 and into a boss 506 contained in functional unit 104A near catch feature 216. The configuration shown advantageously provides for permanent attachment of the units until a user such as a medical technician disengages fastener 500. In this manner, for example, miscellaneous persons around and in the area of the modular patient care system 100 are prevented either from intentionally or accidentally causing disconnection of units.

The unique combination of the module elements described thus far provide for many advantages in stability, safety, security, and ease of use. For example, the attachment of a functional unit may be achieved in a one hand, single step operation, while the presence of latch 218 and catch feature 216 dictate that detachment must take place in a two step operation. This is advantageous in a medical environment where quick, easy attachment of units to the linear array may be necessary, but where detachment of units should be permissible only upon an explicit, reasoned desire of a user and not by accident. This feature is enhanced an a preferred embodiment of the invention employing a fastener 500, wherein further steps are needed to detach modules.

Further, the ease of the one-handed, single step operation in the attachment of units is enhanced where latch 218 and catch feature 216 provide for tactile feedback during the attachment operation. This is advantageous in the medical environment by freeing up the eyes of the user during attachment to pay attention to more sensitive events taking place, such as insuring that needles, lines, fluids, or pumps are not being disturbed during the mechanical movement. Further, the avoidance of the need for visual feedback to the user may save precious moments during medical emergencies when the user's eyes are more advantageously averted to the emergency at hand.

Even further, the presence of male elevation feature 212 mated to recess feature 214 provides for additional front to back stability of the units during handling and abuse. These features also provide guidance during connection to prevent off-axis insertion. Vibration of coupled units is further reduced by the compression of covers 220 and 224 against each other and pockets 222 and 226.

Even further, several means exist to protect the electrical connections from fluid ingress when units are not connected. First, the contact geometry, contact orientation, and hook geometry as shown in FIG. 4 prevent fluid from accumulating on surfaces of the male connector portion 208. Similarly, the contact geometry, contact orientation, and contact location of the electrical contacts 408 prevent fluid from accumulating on surfaces of the female connector portion 210. Use of low surface energy/hydrophobic material for body portions 406 and 412, insert-molding of the contacts 400 and 408, and the presence of covers 220 and 224 further discourage unwanted fluid accumulation and ingress.

In the modular patient care system 100 of FIG. 1, electrical power is supplied to functional modules 104 by interface unit 102. The interface unit 102, in turn, may be powered by conventional methods known in the art. At least one electrical power path exists among the electrical contacts 408 and 400 at the connecting point of any two units.

The goal of a module powering system designed in accordance with the present invention is, first, for interface unit 102 to provide power to any attached module or set of modules by powering immediately adjacent modules. Thus, in FIG. 1, interface unit 102 is to supply electrical power to all functional units 104 by powering functional units 104B and 104C, which each use a portion of this power and which, in turn, transfer at least a portion of this power further down the line to units 104A and 104D, respectively.

Second, the module powering system in accordance with the present invention is to permit lateral interchangeability of the modules, and thus the powering system of any functional unit 104 is to be bilateral. By bilateral, it is meant that the functional unit 104 may receive power from either its first or second side, and may transmit this power, if necessary, to attached units on its second or first side, respectively.

Third, it has been found that a module powering system according to the present invention is to comprise an interface unit 102 and functional units 104 which, if they are positioned on the originating or terminating end of a linear array, do not allow a live voltage to exist at the open electrical contacts which will exist at these ends. Such a requirement provides, for example, for added security of the unit from power failure due to accidental or intentional shorting of the exposed power leads.

Figure 6:
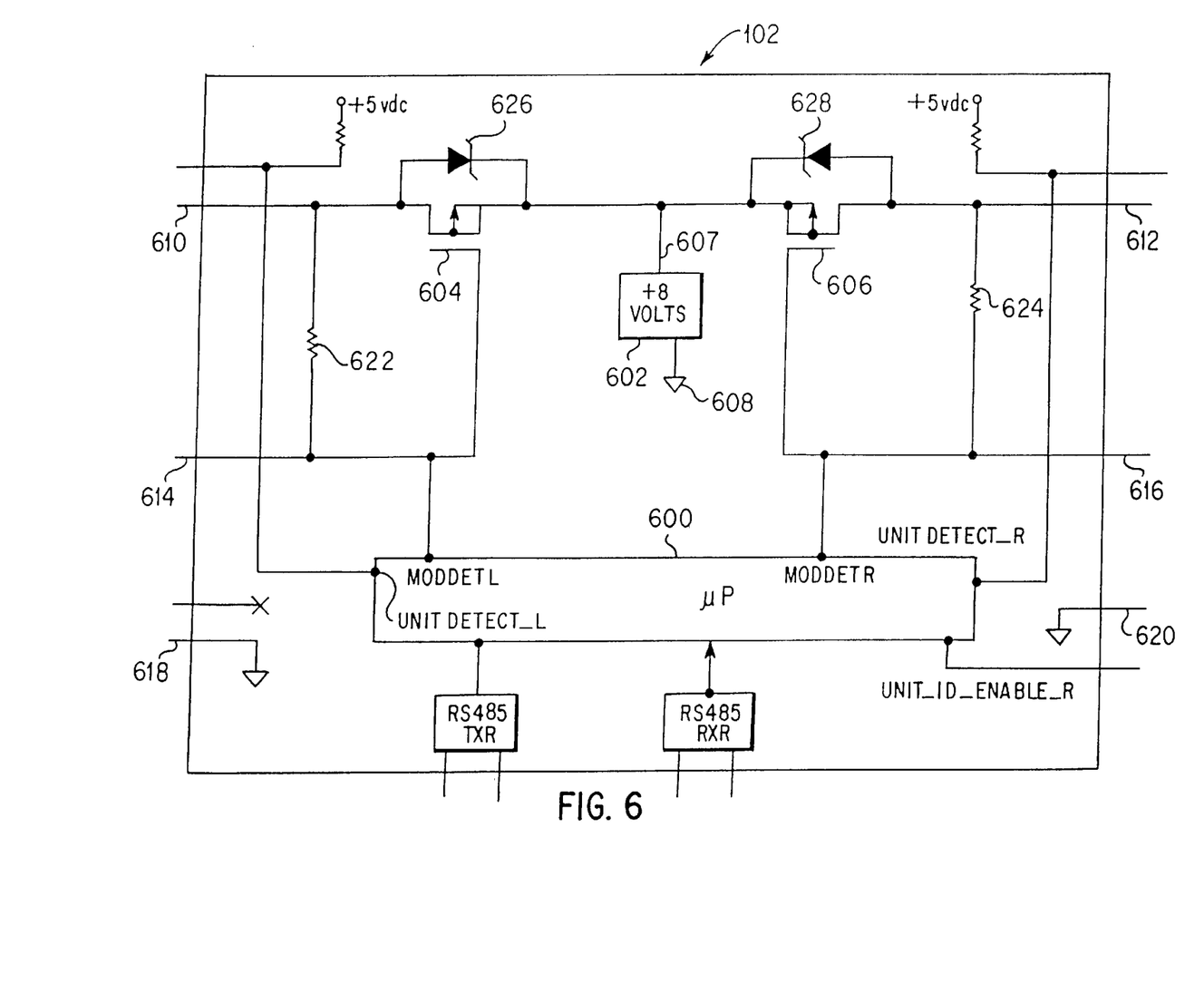
FIG. 6 shows a functional diagram of the power provision features of the interface unit according to the present invention.
Figure 7:
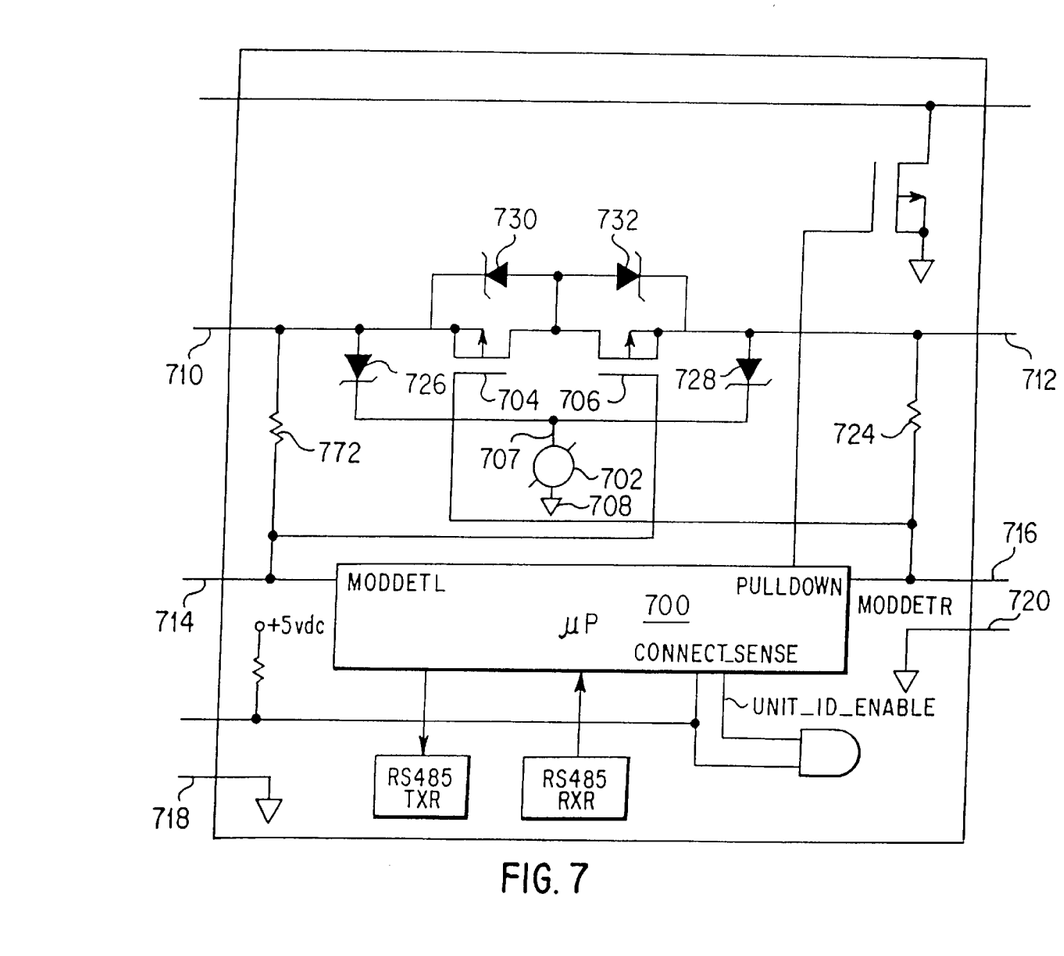
FIG. 7 discloses a functional circuit diagram of the bilateral powering features of a functional unit in accordance with the present invention.
Figure 8:
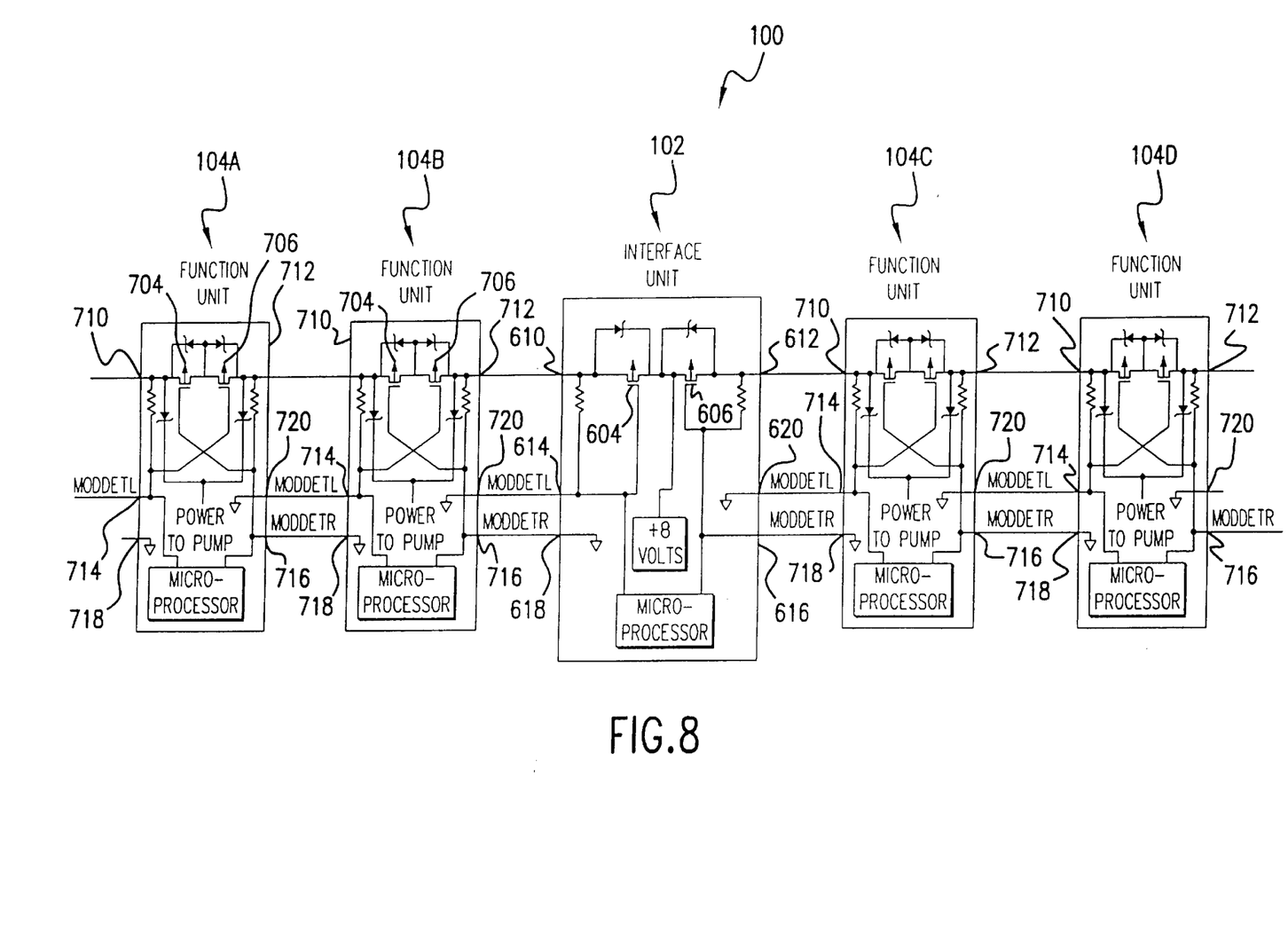
FIG. 8 shows a functional diagram of the unit detection and power features of a modular patient care system in accordance with the present invention.

Turning now to FIGS. 6 through 8, a module powering system according to a second embodiment of the present invention is described. FIG. 6 shows a functional diagram of the power aspects of interface unit 102 designed in accordance with the present invention. Interface unit 102 comprises a microprocessor 600, a power source 602, a left transistor 604, and a right transistor 606. Power source 602 is adapted for providing an 8-volt DC voltage by either generating its own power, as from a DC voltage source such as an internal battery, or for adapting power from an external AC or DC source, as is known in the art. The 8 volts DC provided by power source 602 is provided by lead 607 with respect to the ground plane of interface unit 102, denoted generally by element 608 in FIG. 6. Interface unit 102 further comprises left and right power leads 610 and 612, respectively, for coupling to and providing power to left and right adjacent functional units, respectively, when connected. Power leads 610 and/or 612 will be left open, however, when adjacent units are not connected. Interface unit 102 further comprises left and right module detect leads 614 and 616, respectively, for detecting the presence of attached functional units on the left and right sides, respectively. Interface unit 102 further comprises ground leads 618 to 620 for providing left and right sense signals, respectively (which in this embodiment are ground signals) to adjacently attached units. It is noted that additional electrical contacts not shown may provide an overall ground plane signal to attached functional units, as is known in the art.

As shown in FIG. 6, lead 607 of power source 602 is coupled to the source of left transistor 604 and also to the source of right transistor 606. In the embodiment shown, transistors 604 and 606 are, in this embodiment, P-channel enhancement MOSFETs. The gate of left transistor 604 is coupled to left module detect lead 614, while the gate of right transistor 606 is coupled to right module detect lead 616. Finally, the drain of left transistor 604 is coupled to left power lead 610, while the drain of right transistor 606 is coupled to right power lead 612.

As shown in FIG. 6, transistor 604 will conduct (i.e., create a "short" between its drain and source) when its gate is low with respect to the source, and will not conduct (i.e., create an "open") when its gate is high. Transistor 606 behaves similarly. Thus, if left module detect lead 614 is grounded by attachment to an external signal, such as a signal provided by an attached functional unit to the left, transistor 604 will conduct, and thus power lead 610 will be coupled to power source lead 607 to provide power. When left module detect lead 614 is left open, as when a unit is not attached to the left, transistor 604 does not conduct and leaves power lead 610 electrically isolated from power source lead 607. This, of course, is a desired result. Similar characteristics exist for right module detect lead 616, transistor 606, and right power lead 612.

It is noted that the coupling of the left module detect lead 614 to microprocessor 600 at pin MODDETL shown in FIG. 6 does not affect the powering aspects described here, as pin MODDETL is only for detection purposes of the microprocessor for purposes to be described later. A similar note applies to right module detect lead 616 and pin MODDETR of microprocessor 600. Finally, it is noted that Schottky diodes 626 and 628 are provided across the drain and source of transistors 604 and 606, respectively, for protection against reverse voltages, as is known in the art.

FIG. 7 shows a functional diagram of the power aspects of an exemplary functional unit 104A designed in accordance with the present invention. Functional unit 104A comprises a microprocessor 700 and a load 702 such as an infusion pump motor. It is noted that load 702 may represent any kind of electrical system requiring power, however. Functional unit 104A further comprises a left transistor 704 and a right transistor 706. Load 702 receives electrical power provided between an input node 707 and a ground plane, generally denoted by element 708 in FIG. 7. Functional unit 104A further comprises a left power lead 710, a right power lead 712, a left module detect lead 714, a right module detect lead 716, a left ground lead 718, and a right ground lead 720.

As shown in FIG. 7, the drain of left transistor 704 is coupled to the drain of right transistor 706. Transistors 704 and 706 are, in this embodiment, P-channel enhancement MOSFETS. The source of left transistor 704 is coupled to left power lead 710, while the source of right transistor 706 is coupled to right power lead 712. Left power lead 710 is also coupled through a resistor 722 to the left module detect lead 714, which is in turn coupled directly to the gate of right transistor 706. Correspondingly, right power lead 712 is coupled through a resistor 724 to the right module detect lead 716, which is in turn coupled directly to the gate of left transistor 704. Left power lead 710 is coupled to the cathode of a diode 726 whose anode is in turn coupled to input node 707 of load 702. Likewise, right power lead 712 is coupled to the cathode of a diode 728 whose anode is in turn coupled to the input node 707 of load 702. In this manner, if a positive power voltage is present at lead 710, power is supplied to load 702 without being supplied to lead 712 unless both transistors 704 and 706 are conductive. Likewise, if a positive power voltage is present at lead 712, power is supplied to load 702 without being supplied to lead 710 unless both transistors 704 and 706 are conductive.

As shown in FIG. 7, transistor 704 will conduct (i.e., create a "short" between its drain and source) when its gate is low with respect to the source, and will not conduct (i.e., create an "open") when its gate is high. Transistor 706 behaves similarly. The gate of transistor 704 will be forced low when right module detect lead 716 is grounded by an adjacent attached unit to the right. Correspondingly, the gate of transistor 706 will be forced low when left detect lead 714 is grounded by an adjacent attached unit to the left. It is noted that Schottky diodes 730 and 732 are provided across the drain and source of transistors 704 and 706, respectively, for protection against reverse voltages, as is known in the art. It is noted that, as described above and as shown in FIG. 7, module 104A forms a laterally symmetric powering arrangement.

As described herein, a modular patient care system 100 comprising the interface unit of FIG. 6 and functional modules according to FIG. 7 advantageously provides for bilateral power sourcing and transfer through the functional modules 104, while providing electrical isolation of power leads of units at the originating and terminating ends, respectively.

FIG. 8 shows the modules of FIG. 6 and FIG. 7 arranged in an exemplary arrangement comprising functional unit 104A at the originating (left) end, functional unit 104D at the terminating (right) end, and units 104B, 102, and 104C in the middle, respectively. As shown in FIG. 8, the electrical leads between units are arranged according to the following simple scheme. Left power leads (610 or 710) are coupled to right power leads (712 or 612) in any pair of adjacent units. Left module detect leads (714 or 614) are coupled to right ground leads (620 or 720) in any pair of adjacent units. Finally, left ground leads (618 or 718) are coupled to right module detect leads (716 or 616) in any pair of adjacent units.

Serving as an example of a system according to the present embodiment of the present invention, the powering configuration of the modular patient care system 100 shown in FIG. 8 advantageously functions as follows.

Looking to the left of interface unit 102, lead 720 of unit 104B grounds the gate of left transistor 704 of unit 102 via module detect lead 614. Transistor 604 is turned on, and power is thus supplied through left power lead 610 of unit 102 to right power lead 712 of unit 104B, thus powering the load 702 of unit 104B. Left ground lead 618 of unit 102 grounds the gate of left transistor 704 of unit 104B through right module detect lead 716, making transistor 704 conductive. Further, right ground lead 720 of unit 104A grounds the gate of right transistor 706 of unit 104B, making transistor 706 conductive. The result is that both of transistors 704 and 706 of unit 104B are conductive, and thus power lead 712 of unit 104A will receive power from left power lead 710 of unit 104B. Therefore, load 702 of unit 104A will be powered, and thus left side units 104A and 104B are fully powered.

However, there is no ground signal provided to left module detect lead 714 of unit 104A because it is the leftmost unit. Thus, right transistor 706 of unit 104A remains turned off. The result is that left power lead 710 of leftmost unit 104A is electrically isolated from right power lead 712, which is the desired result. It should be clear to anyone of ordinary skill on the art, given the lateral symmetry of the powering arrangement described above, that right side units 104C and 104D operate in a similar but reflexive fashion to the left side units 104A and 104B. Thus, power is provided to both units 104C and 104D, but right power lead 712 of rightmost unit 104D remains electrically isolated from a power source. This, of course, is the desired result.

Additionally, it should be clear to anyone of ordinary skill in the art that the units 102 and 104A through 104D can be arranged in any order in FIG. 8 with the desired result of (1) powering of all units, (2) electrical isolation of the left power leads 710 or 610 of the leftmost (originating) unit, and (3) electrical isolation of the right power leads 712 or 612 of the rightmost (terminating) unit.

Various embodiments of the invention have been described. The descriptions are intended to be illustrative, not limitative. Thus, it will be apparent to those skilled in the art that modifications may be made to the invention as described without departing from the scope of the claims set out below.

What is claimed is:

1. A modular patient care system having a plurality of units, said plurality of units comprising:
   an interface unit for providing a user interface to said system and for providing electrical power to said system; and
   a functional unit capable of removable connection to said interface unit, said functional unit being capable of providing patient therapies or monitoring, said functional unit comprising a first lead, means for providing a first signal when connected to an adjacent unit, and a load coupled to said first lead for receiving electrical power therefrom;

wherein said interface unit comprises:
   a power source for receiving electrical power from a power supply and providing electrical power to said patient care system;
   a power lead for electrically contacting said first lead, said power lead having an active state when electrically coupled to said power source, said power lead having an inactive state when electrically isolated from said power source;
   detecting means for detecting said first signal;
   coupling means for electrically coupling said power lead to said power source responsive to the presence of said first signal;
wherein said power lead is in the active state when said functional unit is connected to said interface unit for supplying electrical power to said functional unit, and wherein said power lead is in the inactive state when said functional unit is not connected to said interface unit.

2. A modular patient care system, comprising:
an interface unit for providing a user interface to said system and for providing electrical power to said system, said interface unit comprising a power lead; and
a plurality of functional units for providing patient therapies or monitoring, said plurality of functional units including a first functional unit and a second functional unit, said first functional unit being capable of removable connection to said interface unit, said second functional unit being capable of removable connection to said first functional unit and having a first lead, said second functional unit further comprising means for providing a first signal to said first functional unit when connected thereto and a load coupled to said first lead for receiving electrical power therefrom;
wherein said first functional unit further comprises:
   a first lead configured and dimensioned to contact said power lead of said interface unit when said first functional unit is connected to said interface unit;
   a second lead for electrically contacting said first lead of said second functional unit;
   a load coupled to said first lead for receiving electrical power therefrom;
   detecting means for detecting said first signal from said second functional unit;
   means for permitting an electrical coupling of said second lead to said first lead of said first functional unit responsive to said first signal from said second functional unit and for electrically isolating said second lead from said first lead of said first functional unit in the absence of said first signal from said second functional unit;
whereby said second lead is permitted to be electrically coupled to said power lead of said interface unit when said second functional unit is connected to said first functional unit, and electrically isolated from said power lead when said second functional unit is disconnected from said first functional unit.

3. The modular patient care system of claim 1, said interface unit having an originating side and a terminating side, further comprising an array of functional units each having an originating side and a terminating side, wherein the originating side of any unit is capable of connection to the terminating side of any other unit,
   whereby a linear array of units having an originating end and a terminating end is capable of being formed.

4. The modular patient care system of claim 3,
   wherein said first signal is an originating side sense signal for indicating the presence of said functional unit to a unit adjacent said originating side in the linear array;
   wherein said first lead of said functional unit is an originating side lead,
   wherein said power lead is a terminating side power lead for contacting an originating side lead of a functional unit adjacent said terminating side of said interface unit, and
   wherein said detecting means is a terminating side detecting means for detecting an originating side sense signal from the functional unit in the linear array adjacent said terminating side of the interface unit,
   whereby when said functional unit is connected adjacent to the terminating side of said interface unit, said terminating side power lead is in the active state, and
   whereby said terminating side power lead is inactive when no functional unit is connected adjacent to the terminating side of said interface unit.

5. The modular patient care system of claim 4, said functional unit further comprising a terminating side lead, said load also being coupled to said terminating side lead and being capable of receiving electrical power therefrom, said functional unit further comprising a means for providing a terminating side sense signal to a unit adjacent said terminating side when connected thereto, said interface unit further comprising:
   an originating side power lead for contacting a terminating side lead of a functional unit adjacent said originating side;
   an originating side detect means for detecting a terminating side sense signal from a functional unit adjacent said originating side; and
   an originating side coupling means for electrically coupling said originating side power lead to said power source responsive to the presence of said terminating side sense signal;
   whereby when said functional unit is connected to the originating side of said interface unit, said originating side power lead is electrically coupled to said power source, and
   whereby said originating side power lead is electrically isolated when no functional unit is connected to the originating side of said interface unit.

6. The modular patient care system of claim 5, said interface unit further comprising:
   an originating side sense signal providing means for providing an originating side sense signal to a functional unit adjacent said originating side; and
   a terminating side sense signal providing means for providing a terminating side sense signal to a functional unit adjacent said terminating side.

7. The modular patient care system of claim 4, said terminating side detection means comprising a lead designed and configured to contact said originating side sense signal providing means of said functional unit adjacent said terminating side upon attachment.

8. The modular patient care system of claim 7, said terminating side coupling means comprising a transistor having a first terminal coupled to said power source, a second terminal coupled to said terminating side power lead, and a third terminal coupled to said terminating side detection means lead.

9. The modular patient care system of claim 8, said transistor being a MOSFET, said first terminal being the source of said MOSFET, said second terminal being the drain of said MOSFET, and said third terminal being the gate of said MOSFET.

10. The modular patient care system of claim 8, said functional unit further comprising a terminating side lead, said load also coupled to said terminating side lead and being capable of receiving electrical power therefrom, said functional unit further comprising a means for providing a terminating side sense signal to a unit adjacent said terminating side when connected thereto, said interface unit further comprising:
   an originating side power lead for contacting a terminating side lead of a functional unit adjacent said originating side;
   an originating side detecting means for detecting a terminating side sense signal from the functional unit adjacent said originating side; and
   originating side coupling means for electrically coupling said originating side power lead to said power source responsive to the presence of said terminating side sense signal;
   whereby when said functional unit is connected to the originating side of said interface unit, said originating side power lead is electrically coupled to said power source, and
   whereby said originating side power lead is electrically isolated when no functional unit is connected to the originating side of said interface unit.

11. The modular patient care system of claim 10, said originating side detection means comprising a lead designed and configured to contact the terminating side sense signal providing means of the functional unit adjacent said originating side upon attachment of the functional unit to the originating side of said interface unit.

12. The modular patient care system of claim 11, said originating side coupling means comprising a transistor having a first terminal coupled to said power source, a second terminal coupled to said originating side power lead, and a third terminal coupled to said originating side detection means lead.

13. The modular patient care system of claim 6, said originating side and terminating side sense signals being ground signals.

14. A modular patient care system having a plurality of units including an interface unit for providing a user interface to said system and for providing electrical power to said system, said plurality of units also including a plurality of functional units for providing patient therapies or monitoring, said interface unit comprising:
   a left side, a left lead coupled to said left side, and a left signal providing means at said left side;
   a right side, a right lead coupled to said right side, and a right signal providing means at said right side;
   a power source;
   means for coupling said left lead to said power source responsive to a right signal from an attached adjacent left functional unit; and
   means for coupling said right lead to said power source responsive to a left signal from an attached adjacent right functional unit;
wherein each functional unit comprises:
   a left side and a right side, said left side being capable of coupling to the right side of any other unit, whereby said interface unit and functional units are capable of being arranged in a linear array of units having a leftmost unit and a rightmost unit;
   a left lead at left side and a right lead at said right side, said left lead for coupling to the right lead of an adjacent left unit, said right lead for coupling to the left lead of an adjacent right unit;
   a load coupled to said left lead through a left one-way power means and capable of receiving electrical power therefrom, said load also being coupled to said right lead through a right one-way power means and capable of receiving electrical power therefrom;
   a left signal providing means for providing a left signal to an adjacent left unit;
   a right signal providing means for providing a right signal to an adjacent right unit;
   a left detecting means for detecting the right signal of an adjacent left unit;
   a right detecting means for detecting the left signal of an adjacent right unit; and
   means for coupling said left lead to said right lead responsive to the presence of the combination of a left signal from a right adjacent unit and a right signal from a left adjacent unit in the linear array;
   whereby said loads of each functional unit in the linear array are electrically coupled to said power source,
   whereby said left lead of said leftmost unit of said linear array is electrically isolated from said power source, and
   whereby said right lead of said rightmost unit is electrically isolated from said power source.

15. The modular patient care system of claim 14, said left detection means comprising a lead configured and dimensioned to connect to a right signal providing means of an adjacent left unit when connected, said right detection means comprising a lead configured and dimensioned to connect to a left signal providing means of an adjacent right unit when connected.

16. The modular patient care system of claim 15, said means for coupling said left lead to said right lead comprising:
   a left transistor having a first terminal coupled to said left lead, a second terminal, and a third terminal coupled to said right detection means;
   a right transistor having a first terminal coupled to said right lead, a second terminal coupled to said second terminal of said left transistor, and a third terminal coupled to said left detection means.

17. The modular patient care system of claim 15, wherein said left one-way power means comprises a first diode connected between said left lead and an input of said load, and wherein said right one-way power means comprised a second diode connected between said right lead and said input of said load.

18. The modular patient care system of claim 16, wherein said left and right transistors are MOSFETs, the third terminal of said left MOSFET transistor being its gate terminal, the third terminal of said right MOSFET transistor being its gate terminal.

19. A modular patient care system, comprising:
   a plurality of modules including a first module and a second module, said second module comprising a first portion grippable by a user, said second module being configured and dimensioned so as to be capable of being held by a single hand of the user by gripping said first portion;
   a hinge connector pair configured and dimensioned to allow hingeable engagement of said second module to said first module near a first end of said second module;

a latch mechanism for securing said second module to said first module near a second end of said second module, said latch mechanism comprising a first part connected to said first module and a second part connected to said second module near said second end, said second part being capable of springably securing to said first part when forced into said first part;

means for releasing said second part from said first part;

a guide mechanism separate from said hinge connector pair and said latch mechanism and located therebetween, said guide mechanism for discouraging off-axis engagement of said first and second modules and for providing mechanical stability for said first and second modules when engaged;

wherein said means for releasing is located sufficiently distal from said first portion of said second module such that a second hand is required to actuate said releasing means when the first hand of the user is gripping said first portion;

whereby said second module is capable of being structurally engaged to said first module in a one-handed, single step operation, and whereby an at least two-step or two-handed operation is required to structurally disengage said second module from said first module.

20. The modular patient care system of claim 19, said latch mechanism further comprising a latch tongue on one of said first or second parts and a catch feature on the other of said first or second parts for catching and engaging said latch tongue, wherein said releasing means is configured and dimensioned to release said latch tongue from said catch feature upon actuation.

21. The modular patient care system of claim 19, said hinge connector pair comprising:

a male hinge connector on either of said first or second modules, said male hinge connector having a first and second set of electrical contacts formed thereon; and a female hinge connector on the other of said first or second modules for hingeably engaging said male hinge connector, said female hinge connector having a third and fourth set of electrical contacts formed thereon configured and dimensioned to connect to said first and second set of electrical contacts, respectively, upon hingeable engagement of said hinge connector pair;

whereby said first and second modules become electrically engaged upon becoming structurally engaged.

22. The modular patient care system of claim 21, wherein said electrical contacts are configured and dimensioned such that said first and third sets of electrical contacts connect before said second and fourth sets of electrical contacts connect during engagement of said first and second modules, and such that said first and third sets of electrical contacts disconnect after said second and fourth sets of electrical contacts disconnect during disengagement of said first and second modules.

23. The modular patient care system of claim 20, further comprising a fastener for affixing said latch tongue within said catch feature, said fastener being configured and dimensioned such that a special fastener tool is required to release said fastener from said latch tongue, whereby when said fastener has affixed said latch tongue, said first and second modules remain permanently engaged until said fastener is released from said latch tongue using said special fastener tool.

24. The modular patient care system of claim 19, said modules each having a front, a back, and sides, said first and second modules defining a pair when engaged, said guide mechanism comprising:

a male elevation feature protruding from one of said first or second modules;

a female recess feature in the other of said first or second modules;

wherein said male elevation feature is chamfered and said female recess feature is shaped for corresponding lead-in to provide guidance of said modules during engagement.

25. The modular patient care system of claim 20, said latch tongue and said catch feature being configured and dimensioned to provide for springable engagement of said latch tongue into said catch feature sufficient to cause a mechanical resonance at said first portion detectable by the user, whereby tactile feedback is provided to the user upon completion of the engagement of said first and second modules.

26. The modular patient care system at claim 21, said first and second modules defining a pair when engaged, said modular patient care system further comprising a cover coupled to said male or female hinge connectors for covering said connector when not in use, said cover being hingeably adjustable with respect to said connector, wherein said cover is configured and dimensioned to be partially compressed upon engagement of said first and second modules to provide cushion and prevent rattling of said pair.

27. The modular patient care system of claim 21, said first module being a main interface module for providing an interface between the system and the user, said second module being a functional module for providing patient therapies or monitoring, said first and second modules each comprising a face, a first surface, and a second surface opposite said first surface, wherein said hinge connector pair, said latch mechanism, and said guide means are formed at said second surface of said first module and said first surface of said second module, and wherein said second surface of said second module is substantially identical to said first surface of said first module;

whereby said first and second modules are capable of being electrically and structurally engaged by hingeably coupling said first surface of said second module to said second surface of said first module, and whereby said first and second modules are also capable of being electrically and structurally engaged by hingeably coupling said second surface of said second module to said first surface of said first module.

* * * * *

UNITED STATES PATENT AND TRADEMARK OFFICE
CERTIFICATE OF CORRECTION

PATENT NO. : 5,941,846  
DATED : August 24, 1999  
INVENTOR(S) : Duffy et al.

Page 1 of 1

It is certified that error appears in the above-identified patent and that said Letters Patent is hereby corrected as shown below:

Column 1,  
Line 18, after "...Patient Care System," add -- now U.S. Pat. No. 5,836,910 --

Column 16, line 58, thru Column 18, line 59,  
Delete claims 19-27 (canceled per Amendment After Allowance Under 37 CFR § 1.312 filed January 25, 1999, and entered February 22, 1999.)

Signed and Sealed this

Eighteenth Day of September, 2001

Attest:

*Attesting Officer*

NICHOLAS P. GODICI  
*Acting Director of the United States Patent and Trademark Office*